United States Patent [19]

Caetano-Anolles et al.

[11] Patent Number: 5,567,585
[45] Date of Patent: * Oct. 22, 1996

[54] METHOD AND KIT FOR SILVER STAINING, DEVELOPING AN IMAGE AND VISUALIZING BIOLOGICAL MATERIALS

[75] Inventors: Gustavo Caetano-Anolles, Knoxville, Tenn.; Brant J. Bassam, The University of Queensland, Australia; Peter M. Gresshoff, Knoxville, Tenn.

[73] Assignee: The University of Tennessee Research Corporation, Knoxville, Tenn.

[*] Notice: The term of this patent shall not extend beyond the expiration date of Pat. No. 5,492,810.

[21] Appl. No.: 258,553

[22] Filed: Jun. 9, 1994

Related U.S. Application Data

[63] Continuation-in-part of Ser. No. 139,459, Oct. 20, 1993, which is a continuation-in-part of Ser. No. 676,869, Mar. 28, 1991, abandoned.

[51] Int. Cl.$^6$ .............................. C12Q 1/68; G01N 27/26
[52] U.S. Cl. .................. 435/6; 204/462; 204/613
[58] Field of Search ................................ 435/6; 204/182.8

[56] References Cited

PUBLICATIONS

Beidler et al, Analytical Biochem 126:374–380 (1982).
Allen et al, Biotechnique 7:736–743 (1989).
Lomholt et al, Analytical Biochem 164:146–149 (1987).

*Primary Examiner*—W. Gary Jones
*Assistant Examiner*—Eggerton Campbell
*Attorney, Agent, or Firm*—Weiser & Associates, P.C.

[57] ABSTRACT

A silver staining method is provided for staining an organic molecule capable of binding silver. An improved image is developed and visualized. A kit useful in practicing the method is described. A permanent record of the image of the profile of the stained molecules is obtained.

26 Claims, 6 Drawing Sheets

METHOD AND KIT FOR SILVER STAINING, DEVELOPING AN IMAGE AND VISUALIZING BIOLOGICAL MATERIALS

CROSS-REFERENCE TO RELATED CASES

This application is a continuation-in-part of copending application Ser. No. 08/139,459, filed Oct. 20, 1993, which is a continuation-in-part of application Ser. No. 07/676,869, filed Mar. 28, 1991, abandoned which applications are incorporated herein by reference in their entirety.

FIELD OF THE INVENTION

The invention relates to a sensitive and reproducible method for silver staining and visualizing an image (or pattern) of selected biological materials, e.g. nucleic acid fragments, a kit for using the method, the permanent records of the characteristic image of the biological material analyzed and various other embodiments described hereinafter.

BACKGROUND OF THE INVENTION

Modern biotechnological techniques require the visualization of very small amounts of biological materials, for instance, nucleic acids.

Present techniques for visualization of nucleic acid fragments make use of either hybridization probes or direct visualization. Probes utilize radioisotopes which are difficult to handle and have the potential of being detrimental to the health of researchers and the environment.

For direct visualization, silver staining is the preferred method for visualizing an image of nucleic acids in gels.

The silver staining methods currently used fall into one of two categories based on the chemical state of the silver ions that prime the staining reaction. Alkaline methods use a diamine complex of silver nitrate in a highly alkaline environment and usually develop the image in dilute acid solutions of formaldehyde. In contrast, acidic methods use silver nitrate solutions for gel impregnation and usually use alkaline developing solutions containing formaldehyde. Reportedly, alkaline methods are less sensitive, but better suited for thicker gels, whereas acidic methods are more rapid, but work best with thin gels.

The above methods are described in Sommerville, L. L., and Wang, K., *Biochem. Biophys. Res. Commun.*, 102:53–58 (1981); Boulikas, T., and Hancock, R. J., *Biochem. Biophys. Methods*, 5:219–228 (1981); Guillemette, J. G., and Lewis, P. N., *Electrophoresis*, 4:92–94 (1983); Kolodny, G. M., *Anal. Biochem.*, 138:66–67 (1984); Beidler, J. L., Hilliard, P. R., and Rill, R. L., *Anal. Biochem.*, 126:374–380 (1982); Goldman, D., and Merril, C. R., *Electrophoresis*, 3:24–26 (1982); Merril, C. R., Harrington, M., and Alley, V., *Electrophoresis*, 5:289–297 (1984); Blum, H., Beier, H., and Gross, H. J., *Electrophoresis*, 8:93–99; Merril, C. R., Goldman, D., Sedman, S. A., and Ebert, M. H., *Science*, 211:1437–1438 (1981); Heukeshoven, J., and Dernick, R., *Electrophoresis*, 6:103–112 (1985); Nielsen, B. L., and Brown, L. R., *Anal. Biochem.*, 141:311–315 (1984); Allen, R. C., Graves, G., and Budowle, B., *Biotechniques*, 7:736–744 (1989); Rabilloud, T., *Electrophoresis*, 11:785–794 (1990); Merril, C. R., *Meth. Enzymol.*, 182:477–488 (1990); Gottlieb, M., and Chavco, K., *Anal. Biochem.*, 165:33–37 (1987); Heukeshoven, J., and Dernick, R., *Electrophoresis*, 6:103–112 (1985); Wray, W., Boulikas, T., Wray, V. P., and Hancock, R., *Anal. Biochem.*, 118:197–203 (1981) and Switzer, R. C., III, Merril, C. R., and Shifrin, S., *Anal. Biochem.*, 98:231–237 (1979).

Maniatis, T., et al., *Molecular Cloning*, Cold Spring Harbor Laboratory (1982) and Ausubel, F. M., et al., *Current Protocols in Molecular Biology*, Current Protocols (1993), two well-known and standard laboratory reference manuals, disclose silver staining techniques.

A method described in *Molecular Cloning* at pages 18.56 and 18.57 as suitable for silver staining proteins is that of Sammons, et al., *Electrophoresis*, 2:135 (1981) with improvements by Schoenle, et al., *J. Biol. Chem.*, 259:12112 (1984). This method does not include formaldehyde in the impregnating solution, as compared with the method of the invention.

A method in *Current Protocols in Molecular Biology* at page 10.6.5 for silver staining proteins is that of Blum, et al., *Electrophoresis*, 8:93–99 (1987). Blum, et al. does not include formaldehyde in either the impregnating or developing solution, as compared with the method of the invention.

All patents and publications cited herein are incorporated by reference.

The methods of the prior art all have drawbacks which limit their usefulness, e.g., they are less sensitive, have problems with unspecific background, call for numerous steps, and are cumbersome to perform.

The methods of the prior art have also employed a variety of reducing or oxidizing solutions to pretreat gels after fixation of the proteins or nucleic acids to increase the sensitivity and efficiency of silver staining. The method of the present invention does not require a pretreatment of the gels to maintain sensitivity.

SUMMARY OF THE INVENTION

The following describes various embodiments of the invention.

The invention provides an improved method of visualizing an image of a profile characteristic of nucleic acid fragments of various lengths fixed in an acrylamide gel than heretofore known. Unlike the methods of the prior art, the methods of the invention do not require an oxidation or reduction pre-treatment of the gel. Broadly described, the method comprises fixing nucleic acids on a gel, staining the nucleic acids on the gel with a suitable staining chemical, like silver in the presence of an aldehyde, such as formaldehyde, developing the image of the nucleic acids with a suitable developing chemical (or a mixture of such chemicals) like formaldehyde in the presence of carbonate and thiosulfate ions until the image is satisfactorily developed, and stopping the development of the image with a reagent such as acetic acid.

The improved method is highly sensitive, detecting DNA down to less than about 1 pg/mm$^2$ band cross-sections with minimum background staining. Bands of large fragments and fragments of less than 100 nucleotides in length can be visualized. The method is particularly well suited for detecting nucleic acid fragments resulting from the analysis of complex nucleic acid amplification fingerprinting profiles. Such methods are disclosed in publications like Caetano-Anollés, G. and Bassam, G. J. (1993), *Applied Biochem. and Biotech.* 42, 189–200.

The method is suitable for a variety of gels, including "minigels" and sequencing gels, and can assay minute amounts of complex nucleic acid mixtures.

The invention also relates to acrylamide gels which may be treated to provide a permanent record of the image of the characteristic profile of the biological material analyzed.

The acrylamide gels can be of different acrylamide concentrations, with or without denaturing agents, and can be used with various procedures for nucleic acid analysis. Furthermore, the procedure can be used to stain nucleic acids in general, proteins, and polysaccharides, extending its usefulness to other biochemical analyses. The procedure has wide applicability for nucleic acid visualization of animal species, like mammals, and plants.

The method of the invention is well suited as a follow-up of nucleic acid amplification fingerprinting (DAF) or other similar nucleic acid fingerprinting methods such as that disclosed in U.S. Pat. No. 5,126,239 to Livak, et al., which is incorporated by reference herein, or the PCR method as disclosed in U.S. Pat. No. 4,683,202 to Mullis, as well as other PCR patents.

The developed gel film shows an image (or a pattern) characteristic and unique for the nucleic acids—or other biological materials—of the sample analyzed. The image shows lanes with high contrasting bands with respect to the background with the least number of artifacts. The image can be a composite of lanes with bands of different width, intensity and hues of colors, and bands varying in number and width depending on and characteristic of the sample analyzed, which is so accurate that it is reproducible and hence dependable for the same sample under the same conditions. Very closely related prokaryotic and plant isolates, as well as human samples, can be distinguished. The developed and dried (or otherwise preserved) gels provide records of images of the samples analyzed which are the best known to date.

Another aspect of the invention is a kit for the practice of the silver staining method. The kit comprises multiple containers having appropriate amounts of reagents necessary to practice the method as follows: a container containing a suitable silver salt; a container containing an aldehyde solution; a container containing a silver complexing agent; a container containing a carbonate, phosphate or sulfate salt, or a base; a container containing a binding or silanizing reagent; and a container containing a fixer solution.

BRIEF DESCRIPTION OF THE FIGURES

FIGS. 3A–3D show gels stained with prior art staining methods. FIG. 3E shows a gel stained by the method of the invention.

FIG. 6A shows detection by the method of the invention of decreasing concentrations of oligomers 7 and 15 nt in length. FIG. 6B shows migration of a 7-mer mini-hairpin oligonucleotide compared to that of a corresponding non-hairpin oligonucleotide as detected by the method of the invention. FIG. 6C shows migration of 8-mer mini-hairpin oligonucleotides compared to that of a corresponding non-hairpin oligonucleotide as detected by the method of the invention. FIG. 6D shows patterns of a polyacrylamide gel of mini-hairpin nucleotide structures of nucleotides varying in length from 7 to 15.

DETAILED DESCRIPTION OF PREFERRED EMBODIMENTS OF INVENTION

Figure 1:
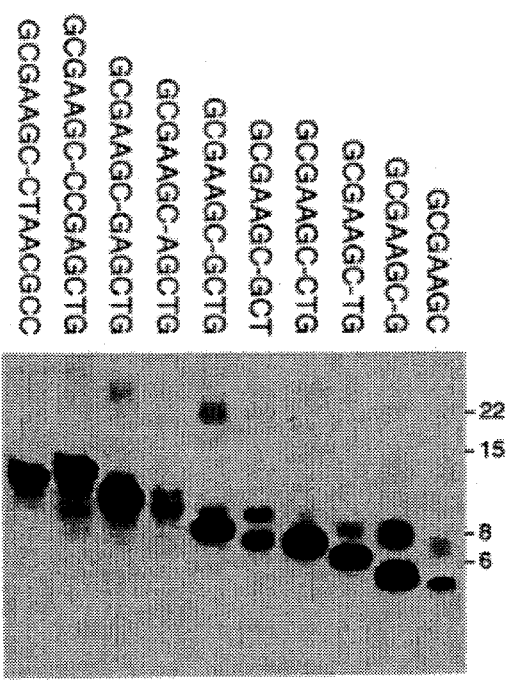
FIG. 1 shows detection by the method of the invention for oligonucleotides of varying sizes.

The method of the present invention is useful to stain and then visualize any organic molecule which is capable of binding silver or a metal equivalent to silver. Such molecules include, but are not limited to, proteins, polypeptides, amino acids, nucleic acids such as DNA and RNA and polymers thereof, lipids, carbohydrates including starches and sugars of various classes, e.g., oligosaccharides, or polysaccharides, such as mucoitin sulfate, lipoproteins, glucoproteins, nucleoproteins, including ribonucleic- and deoxyribonucleic-protein complexes, mucopolysaccharides, e.g., chondroitin sulfate, proteoglycans, mucolipids, such as gangliosides, mucoproteins, and glycolipids.

With regard to the matrix which may be used in the method of the invention, the invention may use virtually any material on or in which the biological molecules, for instance nucleic acids, call be separated or segregated according to size or molecular weight or any other difference which the biological molecules posesses. The method for separating the molecules on or in the matrix can be by electrophoresis techniques, or any other methods which accomplish substantially the same result, like by gravity, pressure (by fluid, e.g., gas or liquid), chromatography, silica gels, whether the method is presently known or not, and whether the materials of the matrix are known or not yet discovered. With rapid advance in techniques, e.g., analytical methods, and apparatuses, it can be readily noted that it is not practical to enumerate the varieties of means which exist to date, or which equivalent means and methods will be developed during the term of this patent that will accomplish the similar purpose of separating the molecules, and then applying some means that will allow the molecules to be distinguished, like a stain or other means. Since means will be used to distinguish the molecules from each other, like a stain, it is common sense that the same means which will be used to distinguish the molecules should not also affect the matrix, e.g., stain the matrix in a way that will interfere or render meaningless the means to distinguish the molecules from each other. For instance, a stain of the molecule should not also stain the matrix, unless a differential staining may be useful.

With further regard to the matrixes, the method typically is useful for staining molecules which have been separated on a matrix using one or two dimensional electrophoresis. The matrix, in which the molecule to be stained is supported, may comprise any material which has been commonly used for gel or thin membrane electrophoretic procedures. For example, the matrix may be derivatized paper, cellulose acetate, cellulose nitrate, starch gel, agarose, Sephadex beads, polyacrylamide, Nylon, glass or glass fiber. Matrixes may vary in thickness from an ultrathin matrix of about 50 microns to about 0.3 mm. For thicker gels, e.g., 1.5–3.0 mm, a carbohydrate-containing matrix is less preferred due to dark background staining. Gel size may be of any convenient length. It may be desirable to attach the matrix onto any suitable backing like polyester, a Nylon mesh, a glass plate, or a plastic sheet for additional support. As is known from standard electrophoretic techniques, the density and pore size of the matrix may also vary. A suitable matrix composition is polyacrylamide, varying from about 50 microns to about 3.0 mm in thickness. A common thickness and size is about 0.45 mm and about 8×10 cm, respectively, which is commonly referred to as a "minigel".

Any material or method suitable for gel or thin membrane electrophoresis may be utilized for the practice of the invention. However, the preferred materials and methods are described hereunder.

The present method may be used to stain DNA sequencing polyacrylamide gels. The concentration of acrylamide used by one of skill in the art to prepare the gel varies with the size of the DNA fragments that are to be analyzed. The concentration of the polyacrylamide will be an amount sufficient for the analysis of the DNA fragments. For this purpose, the concentration of polyacrylamide may vary from about 4% to about 20%.

The length of the polyacrylamide sequencing gel may vary from about 40 cm to about 100 cm. The width may vary from about 20 cm to about 40 cm. Gel thickness may vary from about 0.2 mm to about 0.6 mm, preferably about 0.3 to about 0.45 mm. See Volume 2, page 13.45 from *Molecular Cloning*, Maniatis, T., et al., Cold Spring Harbor Laboratory (1982), incorporated herein by reference.

Gels which are particularly suitable and available are, for instance, sequencing gels like Long Ranger™ Gel (from J. T. Baker), Hydro-Link™ High Performance Gels which are low molecular weight DNA gels for linear separation of 10 to 600 bases (Biochem), gels often referred to as "mini" gels like Mini-Protean II gels (BioRad); agarose gels like 1.D.NA™ Agarose gel (FMC Corporation), Instacryl™ H. Copolymer Agarose gels (International Biotechnologies, Inc., Eastman Kodak Company), Genetic Technology Grade™ Agarose gel (FMC Corporation), which are described in the pamphlets which are incorporated herein by reference. Sequencing gels range in size from about 40 to about 100 cm. Likewise, suppliers in countries foreign to the United States provide such or similar gels.

It is well understood that the method and gels of the invention can be carried out and be part of an automated system, for instance PhastSystem, which provides an electrophoresis work station for automated protein and nucleic acid analysis, which can be applied to SDS and native gradient PAGE, homogeneous PAGE, isoelectric focusing, 2-D PAGE, nucleic acid separation, etc. Other products of PhastGel Chemicals can be considered like the PhastGel Silver Kit (for proteins).

In accordance with the invention, the bands and the profile of composite bands which represent nucleotides of a certain size can be preserved and maintained for any suitable purpose by any suitable preservation technique. In this manner, a permanent record of the profile is produced.

DETAILED DESCRIPTION OF THE PREFERRED METHOD OF THE INVENTION

The following describes steps involved in the silver staining method, materials, amounts of reagents and other variables such as time and temperature of the steps. The following also describes how a permanent record of the analyzed biological materials on the stained gels is obtained.

The invention provides a method for staining a molecule capable of binding silver, which comprises the steps of staining a molecule contained in a matrix with a solution of a suitable silver salt and an aldehyde, developing an image of the molecule with an alkaline reducing solution of an aldehyde and a silver complexing agent, and stopping the development with an appropriate stopper.

The preferred materials and methods are described in detail hereinafter.

With regard to the steps of the silver staining method of the invention, the nucleic acids, while on the selected gel, may be fixed with a convenient and well-accepted chemical, such as aqueous acetic acid. The amount of acetic acid to fix the nucleic acids is not critical. Practice has shown that the amount should be sufficient to fix all (or essentially all) the nucleic acid fragments regardless of size, and yet not in unnecessary excess that could limit detection of all fragments. An acceptable concentration of acetic acid in water ranges from about 1 to 30%, preferably from about 5 to about 20% and more preferably from about 5 to about 15%. The concentration can be adjusted with the size of the nucleic acid fragment analyzed. Time for treatment may be varied from about 2 to 60 minutes, preferably from about 10 to about 20 minutes. The amount can range from 20 to 300 ml or more. One skilled in the art will adjust concentration and time to optimize fixing of the nucleic acids in the gel. For optimally fixing the nucleic acids in the gel, one of skill in the art will know to vary the time of fixing accordingly when using higher or lower concentrations of acetic acid.

Any chemical that accomplishes the function of fixing the molecules e.g., the nucleic acid on the gel, without affecting the integrity or adversely affecting the molecule which is sought to be determined can be used. For instance, an acid which does not hydrolyze the molecule, like a mild organic acid is preferred, typically lower alkanoic acids, etc. The pH preferably should be in the range of about 4.0 to about 5.0.

Following fixing, the gel is washed until all or essentially all of the fixing agent is removed, so as to avoid interference during staining. This can readily be determined. Usually this operation takes about 1 to 5 minutes and can be repeated for shorter, longer or the same periods of time. For this purpose, ultrapure deionized water is particularly suitable.

The method then involves staining the fixed nucleic acid on the gel with a mixture of a solution of silver nitrate and aqueous formaldehyde. The silver may be used in a concentration from about 3 mM to about 20 mM, preferably about 6 mM to about 9 mM. The optimum concentration is that which provides optimum sensitivity.

With regard to the staining of the molecules that are sought to be determined, one skilled in the art will tend to minimize the amount of silver used. The amount of silver will be adjusted depending on the type of target molecule, the thickness and type of matrix, and other parameters. It appears that below about 3 mM the image will tend to be too faint; amounts higher than 9 mM appear unnecessary.

The solution of aqueous formaldehyde in the staining step may vary from dilute formaldehyde of about 10% to about 50%. Conveniently, formaldehyde solutions of about 16% concentration, preferably electron microscopic (EM) or formaldehyde solutions of about 37% concentrations can be used, the first, particularly when staining sequencing gels, the second, particularly when staining "minigels". The concentration of the formaldehyde can range from about 1 ml/l (or less) to about 5 ml/l, preferably about 2 ml/l to about 4 ml/l. When it is desired to use 16% concentration, there may be used from about 2.0 to about 5 ml/l, preferably about 2.5 to about 4.25 ml/l. The staining is performed until optimum staining of the fragments is attained, as can be determined by a few trials and errors. A period of about 10 to 40 minutes, preferably about 20 to 30 minutes is adequate. The concentration of formaldehyde can vary in the range from about 0.001 to about 0.20%, generally from about 0.03 to about 0.09%, more preferably about 0.05 to about 0.06%.

During silver impregnation of the molecule to be stained, the presence of formaldehyde in the silver solution improves sensitivity and contrast. Formaldehyde probably reduces silver at a very low rate, but enough to produce initial nucleation sites around the staining substratum. These sites tend to favor the rapid build-up of silver deposits of development step. In some work related to the invention, optimal staining has been achieved in about 20 minutes. However, 8×10 cm polyester-backed minigels require as little as 10 minutes for high quality staining without significant loss of sensitivity. Impregnation times longer than 90 minutes may affect image loss.

The amount of formaldehyde will be that which will not affect the sensitivity of the method. While its presence is important, the method of detection is more forgiving regarding the actual amount, which can be comparatively less or not critical. It is permissible that the formaldehyde be increased to about 0.4–0.5%.

If any brown residue precipitate is observed due to residual silver after impregnation, a post-impregnation wash with cold water, (preferably ultrapure deionized) may be performed, or alternatively, the developer solution can be used to wash the gel.

In the steps of the method invention, it is preferable to use high purity water which is free of interfering impurities (like metals), such as deionized, e.g., ultrapure distilled water or double distilled water, etc.

The development step of the image of the profile characteristic of the nucleic acids on the gel to be visualized is performed with a solution of a mixture of sodium thiosulfate and of formaldehyde, which reduces the silver ions in an alkaline solution. The pH of the developer is on the alkaline side, as from about 7.0 to about 12.0. The developing solution also contains, for best results, sodium carbonate at a concentration of about 10 to about 50 g/l, generally about 20 to 45 g/l, and preferably about 25–35 g/l. For optimum results for sequencing gels, the sodium carbonate utilized is preferably at least American Chemical Society (ACS) grade. The concentration of sodium carbonate may range from about 1 to about 50%, preferably abut 3 to 9%.

Formaldehyde is generally used in a concentration of about 0.01% to about 0.2%, preferably about 0.055% to about 0.1%. Suitable is about 1 to about 6 ml/l of 16% formaldehyde EM grade. The same volume amounts of 37% formaldehyde are suitable for developing "minigels", preferably about 2.5 ml/l to about 4.25 ml/l for sequencing gels.

The sodium thiosulfate pentahydrate concentration is between about 4 μM to about 130 μM, preferably from about 4 μM to about 30 μM, commonly 4 μM to about 8 μM. With respect to thiosulfate, the amount can be increased to about 130 μM. Any appropriate salt equivalent to thiosulfate may be suitable, like potassium or ammonium thiosulfate.

It is contemplated that the concentration of sodium carbonate may be decreased to below 0.4%, providing this is not to detrimental to image development or higher colored, interfering background. Sufficient sodium carbonate should be supplied to change the pH to the range where reduction will take place.

The pH range of the developing solution can vary in the range of about 6 to about 9. Since the carbonate is in equilibrium with bicarbonate, the solution is actually buffered in the pH range of 6.5 to 8.5, generally 6.5 to about 8.0.

Developing time is generally not so critical as to seriously affect the image. Time can frequently be empirically determined and stopped at optimum image development of the pattern of the lanes, the bands and the color of the background. Generally, the objective is for the colors to be brownish or greyish (dark or light) on a background which under optimum conditions is virtually off-white or white. Some of the colors are sometimes fringed with purple or yellow with reddish lines. The actual color is not determinative but rather the specificity, distinction and demarcation of the bands and lanes of the composite image or pattern.

In the development of the image step, as in most silver staining procedures, image development preferably calls for an abrupt change in pH which will cause the formation of insoluble silver salts. These precipitates attach to the gel surface and decrease image contrast by increasing background staining. Decreasing the concentration of silver on the surface of the gel by prior washing avoids silver precipitation but also decreases sensitivity. However, silver ion complexants, like sodium thiosulfate, decrease the free silver ion concentration, reduce the kinetics of reduction, and thus increase the redox potential in the surrounding matrix, minimizing background staining. A concentration of about 4 μM sodium thiosulfate effectively reduced nonspecific background staining; higher concentrations appear to provide no noticeable advantage.

Decreasing sodium carbonate concentration below the recommended levels (down to about 4 g/l) tends to cause higher background staining and poor image contrast, probably by decreasing the overall rate of silver reduction.

Formaldehyde concentrations between about 0.03–0.11% (by volume) provide an optimal stained image. Lower concentrations tend to have the general effect of reducing sensitivity. In contrast, higher formaldehyde concentrations tend to increase sensitivity but also increase background staining. Higher concentrations also tend to considerably reduce development time, making it difficult to control the staining reaction. Development time is dependent on the components of the developer solution and can vary widely from seconds to minutes. For instance, development time can be made to vary from about 2 to 20 minutes, frequently 8 to 15 minutes.

Higher formaldehyde levels produce bands that are too dark brown-black, while formaldehyde concentrations which are too low produce light brown colors. The size and density of silver grains and the rate of their formation influence the color of the stained bands. Often, the shade of the stained nucleic acid bands is not accurately controllable. However, this does not affect the sensitivity or photographic reproduction.

If overdeveloping has occurred, the gel can be recycled by using a photographic reducer like Farmer's reducer (30% potassium ferricyanide, 60% sodium thiosulfate and 10% sodium carbonate). The gel is cleaned of all reagents, like silver, and the steps of impregnating, developing and stopping are repeated again. Destaining can also be used to darken the bands from brown to purple.

The temperature during development of the image influences the rate of development of the type of image desired. While solutions that are used may be at a starting temperature of about 0° C., or even below, the development temperature is generally maintained in the range of about 1° C. to about 10° C.; for best results a range of about 1° C. to about 4° C., or to about 8° C. or 10° C. depending on the nature of the sample, appears preferable. Temperatures above 10° C. can also be used providing image development be controlled, so as not to proceed too quickly to avoid browning of the gel surface. The temperature, if not controlled, may rise during the development to above the preferred ranges. Temperature requirements may be varied by one skilled in the art depending on gel thickness and the chemical components of the developer.

Especially when using backed gels, temperature during the image developing step is important. While non-backed gels can be stained at room temperature, decreasing temperature helps decrease background staining. Appropriate images developed in backed gels (to either glass or polyester backing sheets) are difficult to obtain with satisfactory results unless temperature is kept within the range of about 8°–12° C. Usually this temperature is that of the developing solution poured at the time of image development. When staining larger gels (like in sequencing applications), heat transfer from the large containers and gel rigs increase the temperature to unacceptable levels for good image development. The outcome is a considerable increase in background staining, in some cases even interfering with information retrieval from sequencing gels. To overcome this problem the developing solution is kept at a lower temperature (about 5° C.) before pouring. A similar situation is encountered when staining miniature gels in the Pharmacia's PhastSystem or like system. Automated silver staining requires the different staining solutions to be pumped through tubing so that they can be delivered to the staining chamber. In this case it was found that optimal image development occurred when the developer was kept in an ice bath (about 0° C.). Delivery of this solution generally increases the temperature to the recommended optimal level.

The development step is carried out for a period adequate to develop the image satisfactorily. Usually about 2 to about 15 minutes, or preferably about 8 to about 12 minutes will be sufficient.

For optimal image development, one skilled in the art may vary one of the concentrations utilized of sodium carbonate, formaldehyde or sodium thiosulfate pentahydrate. The other two chemicals may then be varied accordingly (greater or lesser amounts) to achieve an optimal visualized image of the profile of the nucleic acids.

When optimal image intensity is obtained, the development reaction is stopped by decreasing the pH. To avoid accidental over-development, the reaction should be stopped as quickly as possible. This is best done using cold acetic acid (about 2° C. to about 5° C.) quite suitably from about 6.5 to 8.5% acetic acid or in concentrations which are less than that which might cause image fading. The reaction may be stopped with one of the acid substances which had been used for fixing the nucleic acid or other molecules on the matrix.

It is often desired to make a permanent record of the composite image. Preservation of the image has many advantages. It does not require photography or darkroom facilities. The nucleic acid, e.g., the DNA bands, can be dissected out of dry silver-stained gels and amplified, e.g., using PCR. The record can be preserved, e.g., polyester-backed gels can be maintained for many years by air-drying without suffering distortion or detectable image loss. Non-backed gels can also be preserved, usually between plastic sheets, but may be affected by some distortion from shrinking and handling and require more skill for manipulation.

Another aspect of the invention is a kit. The kit of the invention includes multiple containers containing appropriate amounts of reagents necessary to practice the method.

It is to be understood that the examples and embodiments described herein below are for illustrative purposes only and that various equivalents, modifications or changes in light thereof will be suggested to persons skilled in the art and that such equivalents, modifications or changes are included within the spirit and purview of this application and the scope of the appended claims.

A detailed description of the figures is provided in the examples.

EXAMPLE 1

The method of the invention has been used to obtain gels, from which are visualized a profile of stained bands which represent nucleotides of a certain size previously not achieved.

As shown in FIG. 1, oligomers of less than 25 nucleotides, namely of 22, 15, 8 and 6 nucleotides were separated in polyester-backed 20% polyacrylamide-7M urea 0.45-mm-thick slab mini-gels (8×10 cm). Electrophoresis was at 110 V for 2 h. The dye xylene cyanol FF (which runs at approximately 45 bp) was used to monitor fragment separation. DNA was detected at the pictogram level by the silver staining method of the invention. Backed gels were preserved for permanent record by drying at room temperature. DNA concentrations were measured using a TKO100 fluorometer (Hoeffer, San Francisco, Calif.) by fluorescent enhancement of the dye H33258.

The oligomers were readily visualized and a permanent record of a visualized nucleic acid fragment obtained.

EXAMPLE 2

Figures 2A, 2B:
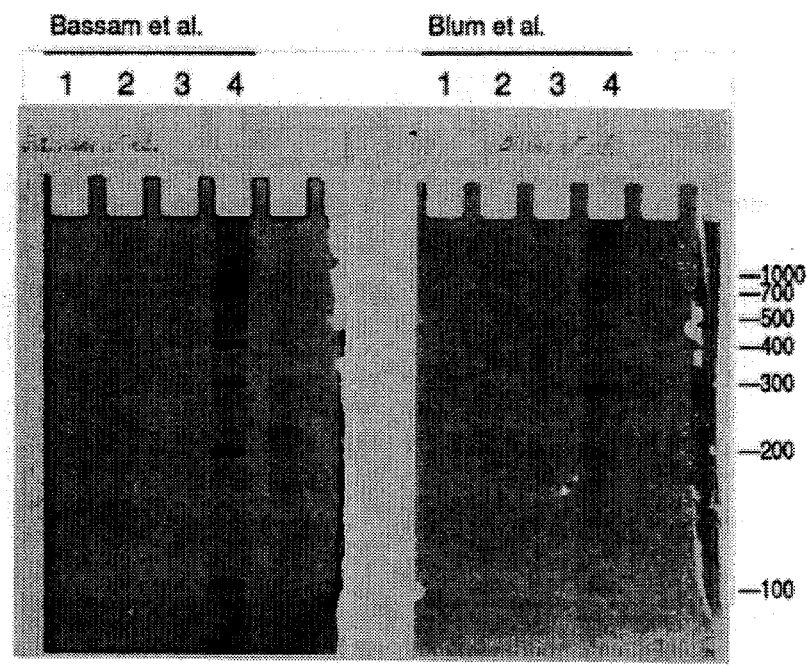
FIGS. 2A–2B show a comparison of stained gels between the present invention and the method of Blum, et al. for visualizing DNA fragments of varying sizes.

FIG. 2 shows a comparison between the silver staining method of the invention and gels obtained and the method of Blum et al., as disclosed in *Electrophoresis* 6:93–99 (1987). Staining conditions are performed as described above.

DNA dilutions were run in a single gel then stained with the procedure of Blum and the invention.

Dilutions of DNA size standards (1000, 700, 500, 400, 300, 200, 100, 50 base pairs shown on the right of panel B) containing 0, 10, 100 or 1000 pg/mm$^2$ of DNA per lane are run in lanes 1, 2, 3 and 4, respectively. The 50 bp fragment ran off the gel.

The results of the comparison are as described hereafter. Lanes 4 of panels A and B contain respectively, 1000 pg of DNA. In panel A, seven black, distinct, well-defined bands on the lane are readily visible. In panel B, the seven bands are less distinct and poorly visible. The background in the gel of Blum, though substantially free of background staining, was so light as to make the bands difficult to read.

One can also detect in lane 2 of Panel A, faint horizontal bands which contain 10 pg/mm$^2$ of DNA total from 0.3 to 3.1 pg/mm$^2$ of DNA fragments ranging from 100 to 1000 bp, respectively. In lane 3 of panel A, which contains 100 pg/mm$^2$ of DNA, the seven bands can be detected, and in lane 4, they are sharp and well defined as noted above.

By comparison, in lane 3 of panel B which contains 100 pg/mm$^2$ of DNA is detected. The bands in lane 4 are, as noted above, appreciably less distinct than the bands on the corresponding lane in panel A.

The terminal dilution for Blum appears in lane 3 which contains 100 pg/mm$^2$ of DNA total. The terminal dilution for the invention appears in lane 2 which contains 10 pg/mm$^2$ of DNA total. This comparison shows that the method of the invention is about 10 times more sensitive than Blum's.

The prior art, typified by Blum, traditionally uses a pretreatment of fixed polyacrylamide gels to improve the sensitivity of the silver stain and accelerate the staining process. The method of the invention does not require such pretreatment.

EXAMPLE 3

Figures 3A, 3B, 3C, 3D, 3E:
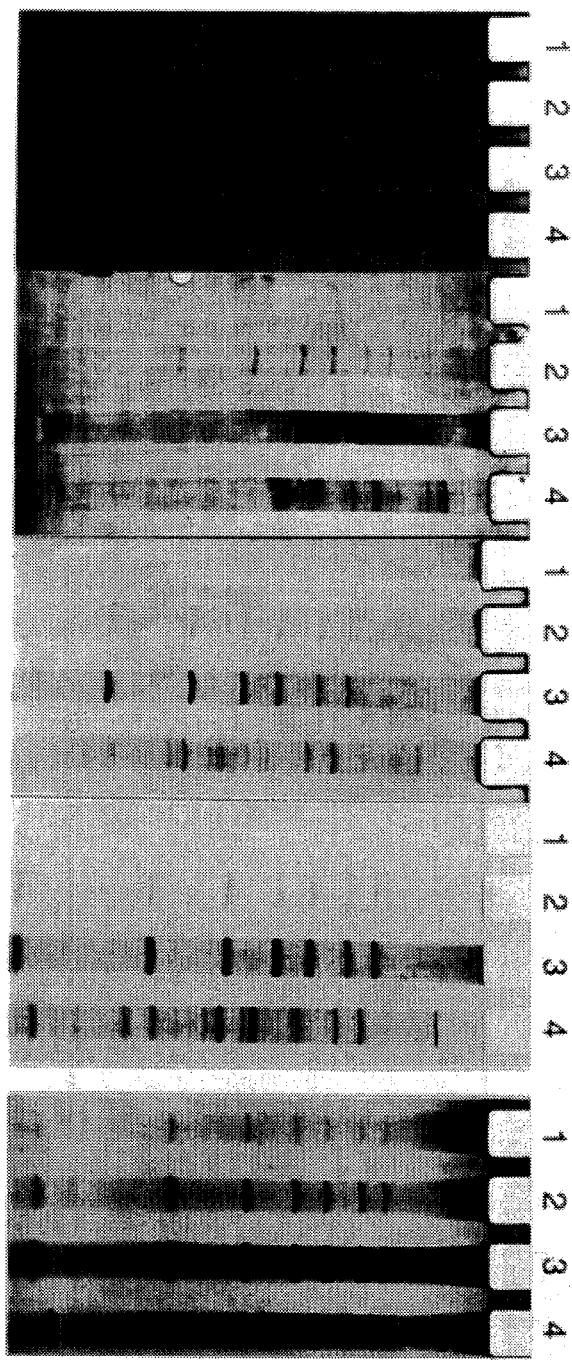
FIGS. 3A–3E show a comparison of stained gels between the present invention and other commercially available silver staining methods.

FIG. 3 shows a comparison between the silver staining method of the invention with various commercial silver staining methods for visualizing characteristic profiles of nucleic acid fragments of varying sizes.

Silver staining kits are available from Polysciences (Warrington, Pa.), Sigma (St. Louis, Mo.), BioRad (Richmond, Calif.) and Boehringer Manheim (Indianapolis, Ind.). The stains were applied following manufacturers instructions.

The commercial methods were the following.

1. Budowle et al., "Analysis of the VNTR Locus D1S80 by the PCR Followed by High Resolution", PAGE, *AM J. Hum. Genet.*, 48, 137–144 (1991). This method is used for forensic applications. Panel A.
2. Gottlieb and Chavco, "Silver Staining of Native and Denatured Eukaryotic DNA in Agarose Gels", *Anal. Biochem.*, 165, 33–37 (1987). Panel B.
3. Switzer, et al., "A Highly Sensitive Silver Stain for Detecting Proteins and Peptides in Polyacrylamide Gels", *Anal. Biochem.*, 98, 231–237 (1979). Panel C.
4. Heukeshoven and Dernick, "Simplified Method for Staining of Proteins in Polyacrylamide Gels and the Mechanism of Silver Staining", *Electrophoresis*, 6, 103–112 (1985). Panel D.
5. Panel E represents an illustration of the method of the invention.

The running conditions were as follows. Replicate samples were run in a 5% polyacrylamide-7M urea gel supported by a polyester film, which was then cut into identical halves. One half was stained with either the protocol of Budowle et al (panel A), Gottlieb and Chavco (panel B), Switzer et al (panel C), Heukeshoven and Dernick (panel D), and the other half stained with the method of the invention (panel E) for comparison. In every instance, image development was stopped when optimal contrast between image and background was obtained. Gel halves were reassembled to avoid photographic bias. Each protocol was repeated at least 4 times and representative results are shown.

The results of the comparison were as follows. The DNA samples were applied in amounts 10 pg of DNA total per lane (lane 1), 100 pg of DNA total per lane (lane 2) and 1000 pg of DNA total per lane (lane 3). Lane 4 contained a complex DNA mixture produced from soybean Glycine soja PI468-397 genomic DNA by DNA amplification fingerprinting using the oligonucleotide GTTACGCC.

Lanes 1 of each one of the panels A–E are compared. It will be seen that on none of the panels can bands be visibly seen as clearly and distinctly as on panel E. Very faint, indistinct bands may be observed in lane 1 of panel A.

In lane 1 of panel E, which contains 10 pg/mm$^2$ of total DNA, there was detected from 0.3 pg/mm$^2$ corresponding to the smallest DNA fragment i.e. 100 bp (lowest on the lane) to 3.1 pg/mm$^2$ corresponding to the 1000 bp DNA fragment.

It is apparent that the method of the invention can detect 1 pg/mm$^2$ of DNA.

Panel A shows a dark grey background with faint black bands in lane 2. Panel B shows bands in lane 2 and 3 indistinctly and inadequately clear. In lane 2, the last band (to the bottom) is indistinct and barely visible. In Panels C and D, the background is very light. Panels C and D show clear bands in lane 3 containing 1000 pg/mm$^2$, which are shown very distinctly in lane 2 of Panel E, containing 100 pg/mm$^2$ of total DNA. Panel E, obtained in accordance with the invention, shows the best image and is the most sensitive method.

EXAMPLE 4

Figure 4:
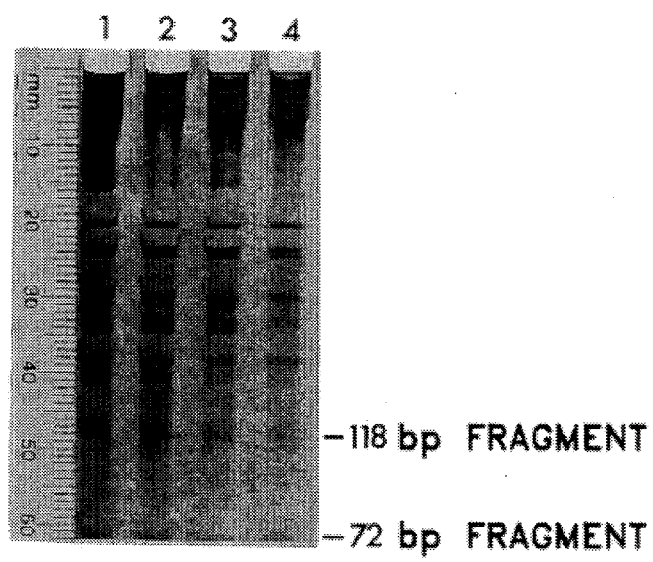
FIG. 4 shows stained gels of nucleic acid fragments of digested φX174 Hae III (118 and 72 bp).

FIG. 4 shows double-stranded DNA fragments from HaeIII endonuclease digests of phage φX174 electrophoresed and stained for profile visualization by the present invention. DNA fragments of 118 bp and 72 bp in length are identified.

All chemicals used for the preparation of buffers and gels were electrophoresis grade (BioRad). Phage φX174 HaeIII restriction digest was purchased from Bethesda Research and pBR322 DNA BstN I digest from New England Biolabs. Ethanol was chemically pure. Formaldehyde and acidic acid were obtained from Mallincrodt, sodium thiosulfate and potassium dichromate from Sigma, silver nitrate from EM Science, and sodium carbonate from Eastman Kodak. All solutions were prepared in deionized water (>10MΩ·m).

Polyacrylamide gel electrophoresis is in 0.45 mm thick slab gels of 5% polyacrylamide and 1.6 or 7 M urea, using a Mini-Protean II cell (BioRad). The ratio of acrylamide to the crosslinker piperazine diacrylamide (BioRad) is 10:1. Gels are cast onto a Gel-Bond PAG polyester backing film (FMC, Rockland, Me.) which is used to support the gel. The gels and the electrophoresis running buffer contain 100 mM Tris·HCl, 83 mM boric acid, 1 mM Na$_2$EDTA at pH 8.3. Nucleic acid samples are applied to the gels in 5-μl aliquots containing 5 M urea and 0.0008% xylene cyanol FF and electrophoresis is at 70 V until the dye front reaches the end of the gel.

EXAMPLE 5

Figures 5A, 5B, 5C, 5D:
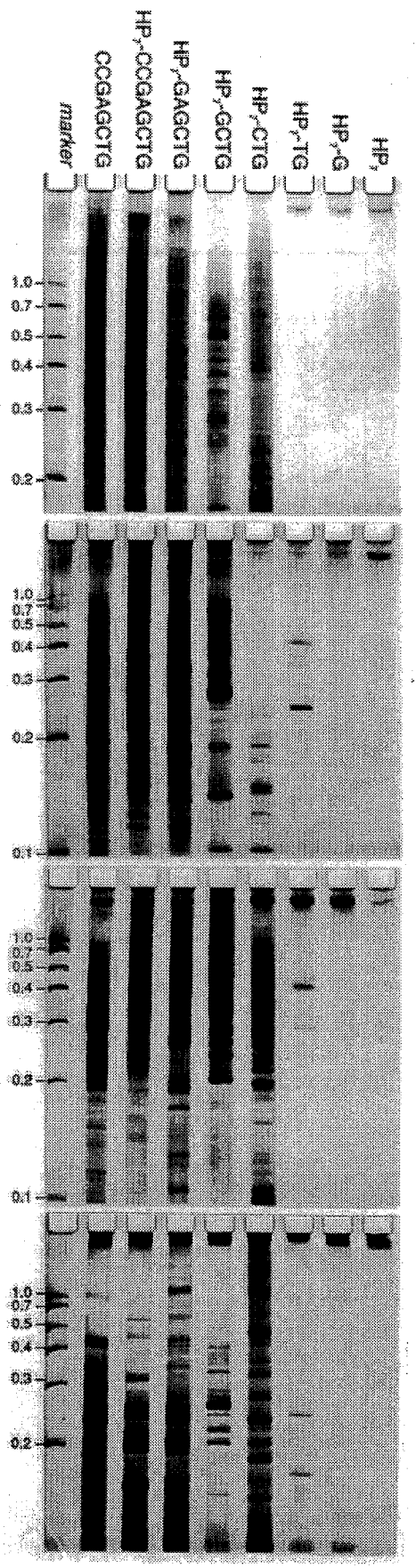
FIGS. 5A–5D show photographs of gels of characteristic profiles of nucleic acids amplified with primers of different lengths which have a "hairpin" of seven nucleotides at the 5" terminus and have a 3" nucleotide sequence varying from none to 8 nucleotides in length, and an 8 nucleotide primer, which gels have been stained by the method of the invention.

FIG. 5 shows the use of sequence related primers having at the 5' end a mini-hairpin (HP7) of sequence GCGAGC for the amplification and staining of DNA. Coupled with the silver staining method of the invention that detects DNA at the picgram level, DNA amplification fingerprinting (DAF) produces characteristic and complex information-rich DNA profiles or images of organisms from bacteriophage to mammals using e.g., polyacrylamide gel electrophoresis.

Panel A shows amplification of DNA from indonesian fruit bat (*Pteropus Hypomelanus*), soybean (Glycine max cv. Bragg) (Panel B), bacterium (*E. coli* strain Smith92) (Panel C), and bacteriophage (Lambda cI857indlSam7) (Panel D). Marker sizes are shown in kilo-bp.

DNA amplification fingerprinting using arbitrary minihairpin oligonucleotide primers is carried out as follows. A modified primer is used to amplify arbitrary stretches of DNA from a DNA template using primers of related sequences as shown in FIG. 4, having at the 5' end a mini-hairpin (HP7) of sequence GCGAAAGC. The method used is as follows: DAF reactions are performed in a total volume of 20–25 μl containing 3 μM primer, 0.3 units/μl AmpliTaq Stoffel DNA polymerase (Perkin-Elmer/Cetus, Norwalk, Conn.), 200 μM of each deoxynucleoside triphosphates, 4 mM MgSO$_4$, 10 mM KCl, 4 mM (NH$_4$)$_2$SO$_4$, 0.1% Triton, 20 mM Tris-HCl (pH 8.3), and about 0.1 ng/μl of template DNA. The mixture is amplified in 35 cycles of 30 s at 96° C., 30 s at 30° C., and 30 s at 72° C. in a recirculating hot-air thermocycler (Bios, New Haven, Conn.). Amplification products are separated in polyester-backed 5% polyacrylamide-urea minigels and stained with silver by the method of the invention. Wells are loaded with 3 µl of a ⅒ dilution of each amplification reaction mixed with 3 µl of loading buffer (5 M urea and 0.02% xylene cyanol FF) and run at 100 V for about 80 min. The method of the invention detects amplified DNA at the picgram level.

EXAMPLE 6

Hairpin structures are postulated to occur in nucleic acid regions with palindromic sequences. For example, short DNA segments can form extraordinarily stable hairpins, consisting of a loop of 2–3 nucleotides (nt) and a 2 nt stem. These "mini-hairpins" have high melting temperatures, unusually rapid mobilities during electrophoreses in polyacrylamide gels, and cause band compression during Maxam-Gilbert DNA sequencing. Mini-hairpins have been observed in natural DNA, such as in the replication origin of page G4 or in rRNA genes. Arbitrary oligodeoxiribonucleotides having mini-hairpin structures at the 5' terminus have been used to prime DNA polymerase-mediated amplification and fingerprint genomic DNA, cloned DNA fragments and PCR products. In studies in conjunction with this invention, denaturing polyacrylamide gel electrophoresis (PAGE) and a sensitive silver stain were used to resolve DNA oligomers and detect alternative molecular species formed by mini-hairpin primers used in DNA fingerprinting studies.

Figure 6A:
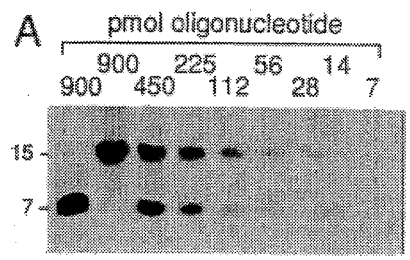
FIGS. 6A–6D shows detection of various oligomers of different sizes.

Silver staining detected oligodeoxiribonucleotides with high sensitivity. Oligomers 7 and 15 nt in length were serially diluted and separated by denaturing PAGE. Approximately 14 and 11 ng/mm$^2$ band cross section (using 0.45 mm thick gels) of DNA (14 and 7 pmol) were detected for the 15-mer and 7-mer, respectively (FIG. 6A). This is 20-to-40-fold less than the amount detected by the fluorescence agent F254 and almost 100-to-500-fold less than that detected by ethidium bromide staining. In contrast, silver staining of larger DNA fragments ($\geq$100 nt) is about 1000-fold more sensitive.

Figures 6B, 6C:
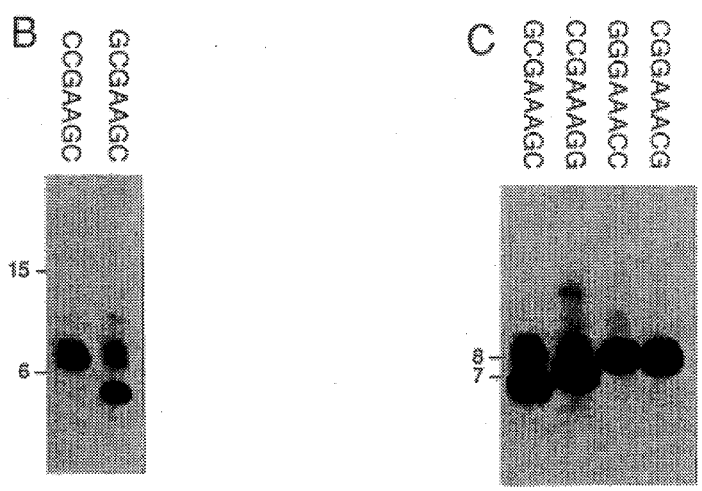
Figure 6D:
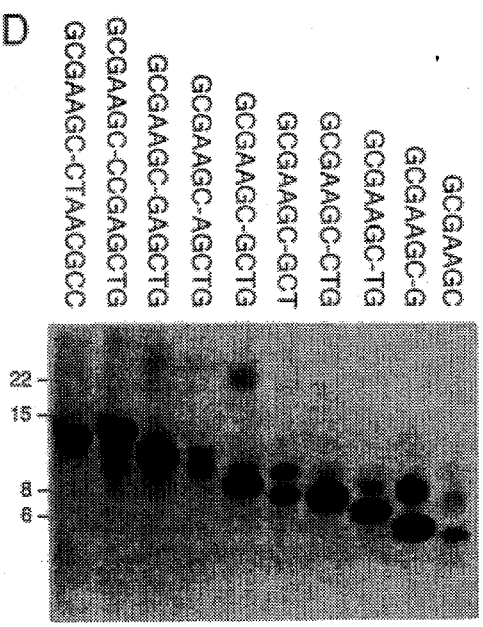

The mobility of mini-hairpins GCGAAGC and GCGAAAGC was appreciably higher than that of their 5' one-nucleotide-lacking fragments incapable of forming hairpin stems (FIGS. 6B and 6C). These two mini-hairpins are especially interesting because they exhibit an extraordinarily high melting temperature (76.5° C.) when compared to a series of stable mini-hairpins containing a loop with 3 and 4 nt. Similarly, the existence of hairpin structures formed on the 5' terminus of a set of arbitrary primers was confirmed by their abnormal rapid electrophoretic mobilities in polyacrylamide gels (FIG. 6D).

Silver staining detected alternative molecular species. Some mini-hairpin primers presented various conformations including alternative hairpin structures, the single strand unimolecular species, and in some cases a bimolecular duplex form. For example, the single stranded species is clear in GCGAAGC (FIG. 6B), GCGAAAGC (FIG. 6C), GCGAAGC-G and GCGAAGC-GCT (FIG. 6D). The duplex structure with an internal loop, especially evident in GCGAAGC-GCTG and GCGAAGC-GAGCTG (FIG. 6D), appears favored in oligomers harboring 3 nt long palindromes. Alternative forms appear to result from slow interconversion of oligonucleotide species. Formation of single strand and duplex forms is also dependent on relatively high DNA concentrations and ionic strengths, a characteristic that minimizes their role during DNA amplification.

Detection of various conformers in denaturing PAGE was surprising, since the same oligomers labeled at the 5' terminus with [$\gamma^{32}$P]dATP using T4-polynucleotide kinase produced only one electrophoretic species. In turn, non-denaturing PAGE revealed conformers only when relatively high oligomer concentrations (5–10 fold higher than in the present experiments) were used. Silver staining and denaturing PAGE are thus well suited for studying intra- and inter-oligomer molecular interactions, probably because of its high sensitivity.

EXAMPLE 7

Several soybean cultivars including Jackson and Williams using a simple sequence repeat (SSR) identified by M. S. Akkaya and P. B. Cregan (USDA/ARS, Beltsville, Md.). The amplification products containing this SSR ranged between 132–190 bp in length. Samples were identified clearly by silver staining after being separated in PAGE-7 M urea in sequencing gels.

EXAMPLE 8

The reagents for the silver staining procedure are assembled into a kit for marketing to qualified individuals to perform the staining procedure. The kit comprises at least four containers, one of each having an appropriate amount of a suitable silver salt, a suitable aldehyde, a suitable silver complexing agent, such as thiosulfate, and a binding or silanizing reagent.

A suitable kit for practicing the method of the invention includes a container for the thiosulfate, for the formaldehyde, and a container for the sodium carbonate. The silver nitrate can be supplied in a sealed, impermeable, aluminum foil envelope. The reagents are provided in suitable amounts, generally for the number of samples to be analyzed. Any reagent which is used twice, like formaldehyde, can be supplied in a graduated or otherwise marked ampule or other container. The kit will normally include instructions for combining the reagents in accordance with the protocol of the method of the invention.

A preferred kit composition is one designed to stain 10 gels which are about 0.45 mm thick and about 8 cm×10 cm in length. One container contains about 10 to about 20 grams of silver nitrate. Another container contains about 60 to about 100 ml of 16 or 37% formaldehyde. Another container contains about 5 to 15 ml of about 1 to about 10% sodium thiosulfate. Another container contains about 10 to 50 ml of about 3 to about 5% sodium carbonate. Another container contains about 500 µl to about 1 ml of gamma—methacryloxypropyltrimethoxysilane (Bind Silane).

Those skilled in the art should note that the disclosure of particular embodiments of the present invention is exemplary only, and that various other alternatives, adaptations, and modifications may be made within the scope of the present invention. The present invention is not limited to the specific embodiments illustrated.

The method of the invention is carried out as described herein above, analyzing DNA fragments in samples shown in the foregoing examples.

DISCUSSION OF ADDITIONAL AND ALTERNATIVE FEATURES OF THE INVENTION

Other suitable fixing agents that may be used are alcoholic solution of polyethylene glycol or polyoxyethylene alkylphenol, a solution of methanol or ethanol and acetic acid, or glutaraldehyde. A suitable alcohol for the alcoholic fixing solution may be one of the following including lower alcohols and preferably linear or branched alcohols having from 1 to 4 carbon atoms. Examples of such linear or branched alcohols include methanol, ethanol, propanol, isopropanol, butanol, isobutanol, and mixtures thereof.

Examples of washing agents are 10% ethanol or methanol: water: acetic acid in a ratio of 5:4:1.

Examples of other suitable silver salts for the impregnating solution include silver chloride and silver acetate. In general, the salts which will dissociate in water to give free silver ions and which will not complex with the reducing agent employed in the method. See, for instance, U.S. Pat. No. to Adams et al. 4,434,234 which is incorporated herein by reference.

Examples of other suitable aldehydes are acetaldehyde, n-butyraldehyde, or glutaraldehyde.

Examples of compounds, other than aldehydes, which may be used in combination with a silver salt are or 5:4:1 methanol: water: acetic acid, or a compound of the formula R-$NH_2$ and a caustic alkali, wherein R-$NH_2$ represents ammonia or a primary amine. Compounds of the formula R-$NH_2$ include, for example, ammonia, ethanolamine, propanolamine, isopropanolamine, butanolamine, isobutanolamine, tris(hydroxyethyl)aminomethane, methylamine, ethylamine, propylamine, butylamine, isobutylamine, etc. Examples of the caustic alkali include sodium hydroxide, potassium hydroxide, etc.

Other examples of suitable components of the alkaline or reducing developing solution are a base, such as aqueous potassium hydroxide or sodium hydroxide, or a salt of sodium phosphate, sodium or potassium carbonate, and an aldehyde such as acetaldehyde, n-butyraldehyde, or glutaraldehyde, and any known silver complexing agents. Alternatively, a dilute acidic solution of about 1% citric acid may substitute for the alkaline or reducing solution.

For stopping the development of the image, citric acid is suitable, as well as any number of other suitable reagents.

One skilled in the art would normally not overlook that resolution with and flexible possibilities of polyacrylamide gel electrophoresis (PAGE) has led to its widespread use for the separation of proteins and nucleic acids. Gel porosity can be varied over a wide range to meet specific separation requirements. One important parameter lies in the polymerization of the polyacrylamide gels. These are formed by co-polymerization of acrylamide and bis-acrylamide (N, N'-methylene-bis-acrylamide). The extent of polymerization as well as other variables such as the choice of crosslinkers will be considered by one skilled in the art to optimize the gel for the purpose intended. Common crosslinkers include DATD (diallyltartardiimide), DHEBA (dihydroxy thylene bis acrylamide), and BAC (bis-acrylylcystamine). See Bulletin 1156, Bio-Rad Laboratories, which is incorporated herein by reference. Further, for other catalysts for polyacrylamide gel polymerization see "Catalysts for polyacrylamide gel polymerization and detection of proteins by silver staining", by Hochstrasser and Merril, in *Applied and Theoretical Electrophoresis* (1988). 1, 35–40. The authors report that the crosslinker diacrylyl-piperazine produces polyacrylamide gels which improved electrophoretic separation of proteins and better physical strength. This publication is included herein by reference. For further improved resolution for two dimensional protein electrophoreses, see "Methods for Increasing the Resolution of Two-Dimensional Protein Electrophoresis", by Hochstrasser et al., *Analytical Biochemistry* 173, 474–435 (1988).

It is known that residual background staining is caused by the catalytic reagents utilized in the polymerization of acrylamide gels. A commonly used catalyst system, tetramethylethylenediamine and ammonium persulfate, was shown to be responsible for the yellow staining background found after a prolonged development time with silver staining. The crosslinker dimethylpiperazine produces polyacrylamide gels which display improved electrophoretic separation of proteins and physical strength. The crosslinker also produces gels with improved detection of proteins by ammoniacal silver staining by reducing the background. See Hockstrasser et al. cited above.

Generally, it is highly advisable that the matrix be prepared prior to staining. The methods are known. See for instance U.S. Pat. No. to Adams et al. 4,434,234 which is incorporated herein by reference. In this manner, unwanted chemicals like urea and buffer which tend to interfere with the silver staining are removed.

The term "visualization" includes all those ingredients and components which are essential for photoimaging of the electrophoretically separated entities, e.g. proteins, nucleic acids and the like.

As discussed herein above for the amount of the reagent, the concentration of the reagent, and the time for performing the discussed steps are optimums for generally obtaining the best results. One skilled in the art, if satisfied with less than optimal results, may operate outside of one or more of the above taught ranges, with one or more of the above disclosed reagents and/or further for a period of time different from that set forth above. Accordingly, this invention contemplates carrying out the method under conditions which are not set forth above as those optimum for best results.

For obtaining optimal results by the method of the invention, the following guidelines are suggested It is preferable not to decrease the recommended time of exposure to acetic acid in the fixing step, as this may cause a poorer image development. It is also preferable not to increase the recommended time of exposure to acetic acid, as this may cause a fading of the bands. However, higher concentrations of acetic acid and longer time periods of fixation may be used, if desired.

It is preferable not to reduce the silver concentration during the impregnating step, as this may cause a tendency to adversely affect sensitivity and contrast. It is preferable not to impregnate for longer than about 90 minutes, as this may be a tendency to cause undesirable image loss.

It is preferable not to reduce the sodium carbonate concentration below optimal levels during the development step, as this cause a higher background staining and poorer image contrast. Higher formaldehyde concentrations enhance sensitivity and reduce developing time, but also tend to increase background staining. It is preferable not to carry out the development at temperatures above 10° C., as this may cause overdevelopment and brown the gel surface due to accelerated development of the image.

It is preferable to stop the development as rapidly as possible to minimize accidental overdevelopment. It is preferable not to use lower than recommended concentrations of acetic acid, so that the reaction may be stopped as rapidly as desired. It is preferable not to use higher than recommended acetic acid concentrations (e.g., above about 10%) for stopping the reaction, as this may cause image fading at such higher concentrations.

The invention includes within its scope all variants which bring about substantially similar or better results.

What is claimed is:

1. An improved method of visualizing an image of a profile characteristic of nucleic acid fragments of various lengths on an electrophoresed gel with more accurate image development and improved sensitivity of detection of the nucleic acids fixed on the washed gel without oxidation or reduction pre-treatment of the gel which method comprises
   a) staining the washed gel having the nucleic acids fixed thereon with a solution of silver comprising silver nitrate an a concentration of about 3 mM to about 20 mM and formaldehyde at a concentration of about 0.001% to about 0.010%,
   b) developing the image of the profile of nucleic acids fixed on the gel with a developing solution which comprises sodium carbonate at a concentration of about 10 g/l to about 50 g/l, formaldehyde at a concentration of about 0.01 to about 0.2%, and sodium thiosulfate pentahydrate at a concentration of about 4 µM to about 130 µM, and
   c) stopping the development by lowering the pH of the image.

2. The method of claim 1 wherein the developing is carried out an a temperature between about 1° C. to about 12° C.

3. The method of claim 2 wherein the developing temperature is between about 4° C. to about 10° C.

4. The method of claim 2 wherein the silver nitrate concentration is from about 3 mM to about 9 mM.

5. The method of claim 4 wherein the silver nitrate concentration is from about 6 mM to about 9 mM.

6. The method of claim 2 wherein the formaldehyde concentration in the staining solution is about 0.01% to 0.2%.

7. The method of claim 6 wherein the formaldehyde concentration in the developing solution is between about 0.05% to about 0.10%.

8. The method of claim 2 wherein the sodium thiosulfate pentahydrate concentration in the developing solution is about 4 µM to about 8 µM.

9. The method of claim 2 wherein the sodium carbonate concentration in the developing solution is about 25 g/l to about 35 g/l.

10. The method of claim 2 wherein the time for staining ranges from about 10 to about 40 minutes.

11. The method of claim 10 wherein the time for staining ranges from about 20 to about 30 minutes.

12. The method of claim 2 wherein the time for developing ranges from about 2 to about 15 minutes.

13. The method of claim 1 wherein the gel is a back-supported gel.

14. The method of claim 13 wherein the back-support is a polyester film.

15. The method of claim 14 which comprises drying the polyester-backed gel and producing a permanent record of the image characteristic of the nucleic acid fragments.

16. The dried polyester-backed gel which is the product of the method of claim 15, which gel is a permanent record of the image characteristic of the nucleic acid fragments, which image comprises a band containing between 0.3 and 3.1 pg/mm$^2$ of the nucleic acid.

17. The electrophoresed polyacrylamide gel of claim 16 which is a permanent record of the image characteristic of nucleic acid fragments of various lengths as shown in lanes 2 through 6 (starting from the marker lane) of panels A through D as shown in FIG. 4.

18. The electrophoresed polyacrylamide gel of claim 16 which is a permanent record of the image characteristic of nucleic acid fragments of various lengths of a size less than 50 nucleotides in length.

19. The gel of claim 18, which is characteristic of nucleic acid fragments of various lengths of a size less than 25 nucleotides in length.

20. The gel of claim 18 wherein the fragments comprise fragments which are not more than 10 nucleotides in length.

21. A method for visualizing an image of a profile characteristic of nucleic acid fragments of various lengths on an electrophoresed gel which comprises staining the nucleic acids fixed on a washed gel with silver ions, developing the image of the fixed nucleic acids on the gel with a buffered solution which comprises sodium carbonate, formaldehyde and sodium thiosulfate pentasulfate, and stopping the image development by lowering the pH, which method comprises the improvement of staining the fixed nucleic acids on the washed gel without oxidation or reduction of the gel.

22. A kit for developing a characteristic pattern of nucleic acid fragments of a sample by silver staining the nucleic acids which comprise a container which contains about 10 to about 20 grams of silver nitrate, a container which contains about 60 to about 100 ml of 16 or 37% formaldehyde, a container which contains about 5 to about 15 ml of about 1 to about 10% sodium thiosulfate and a container which comprises about 10 to about 50 ml of about 3 to about 5% sodium carbonate.

23. A kit of claim 22 wherein the container contains about 1.5 to about 3.5 ml of 37% to 16% of formaldehyde, about 30 g of sodium carbonate and about 0.2 g of sodium thiosulfate.

24. A kit of claim 22 which comprises a label or an insert for the article which specifies a protocol for carrying out the silver staining method on a selected sample with the reagents in the containers.

25. The article of claim 22 which comprises a container containing a pH lowering stop solution.

26. A kit for developing a characteristic pattern of nucleic acid fragments of a sample by silver staining the nucleic acids which comprise a container which contains silver nitrate, a container which contains formaldehyde, a container which contains sodium thiosulfate, a container which contains sodium carbonate and a container which contains a pH lowering stop solution.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GCGAAGCCTA ACGCC                                                    15

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GCGAAGCCCG AGCTG                                                    15

( 2 ) INFORMATION FOR SEQ ID NO:3:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GCGAAGCGAG CTG                                                      13

( 2 ) INFORMATION FOR SEQ ID NO:4:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GCGAAGCAGC TG                                                        12

( 2 ) INFORMATION FOR SEQ ID NO:5:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GCGAAGCGCT G                                                          11

( 2 ) INFORMATION FOR SEQ ID NO:6:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear (x i) SEQUENCE DESCRIPTION: SEQ ID NO:6:

GCGAAGCGCT                                                                                                              10

(2) INFORMATION FOR SEQ ID NO:7:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (x i) SEQUENCE DESCRIPTION: SEQ ID NO:7:

GCGAAGCCTG                                                                                                              10